United States Patent
Thermitus et al.

(10) Patent No.: US 9,939,396 B2
(45) Date of Patent: Apr. 10, 2018

(54) 3D DIFFUSIVITY

(71) Applicant: Netzsch-Gerätebau GmbH, Selb (DE)

(72) Inventors: Marc-Antoine Thermitus, Burlington, MA (US); Martin Brunner, Konradsreuth (DE); Juergen Blumm, Selb (DE); Robert Campbell, Duxbury, MA (US); Thomas Denner, Selb (DE); Michael Gebhardt, Selb (DE); Andreas Hartinger, Röslau (DE); Thilo Hilpert, Selb (DE); Stefan Lauterbach, Selb (DE); André Lindemann, Merseburg (DE); Matthias Schödel, Schwarzenbach (DE); Andreas Strobel, Auerbach (DE); Jürgen Tschöpel, Arzberg (DE)

(73) Assignee: Netzsch-Gerätebau GmbH, Selb (DE)

( * ) Notice: Subject to any disclaimer, the term of this patent is extended or adjusted under 35 U.S.C. 154(b) by 572 days.

(21) Appl. No.: 14/610,726

(22) Filed: Jan. 30, 2015

(65) Prior Publication Data
US 2016/0223479 A1   Aug. 4, 2016

(51) Int. Cl.
*G01N 25/18*   (2006.01)

(52) U.S. Cl.
CPC .................. *G01N 25/18* (2013.01)

(58) Field of Classification Search
CPC .................................................. G01N 25/18
See application file for complete search history.

(56) References Cited

U.S. PATENT DOCUMENTS

| | | | | |
|---|---|---|---|---|
| 4,059,982 A | * | 11/1977 | Bowman | G01F 1/68 374/44 |
| 4,551,030 A | * | 11/1985 | Luukkala | G01B 7/06 250/338.1 |
| 5,376,793 A | * | 12/1994 | Lesniak | G01N 25/72 250/330 |
| 5,713,665 A | * | 2/1998 | Kato | G01N 25/18 374/43 |
| 5,934,140 A | * | 8/1999 | Jackson | G01N 33/346 250/559.27 |
| 6,273,603 B1 | | 8/2001 | Cheindline et al. | |
| 6,375,349 B1 | * | 4/2002 | Gaal | G01N 25/18 374/12 |

(Continued)

OTHER PUBLICATIONS

LFA 447 NanoFlash®—product description and information, Sep. 2012; 12 pages.

*Primary Examiner* — Lisa Caputo
*Assistant Examiner* — Philip Cotey
(74) *Attorney, Agent, or Firm* — Whitmyer IP Group LLC

(57) ABSTRACT

A system for measuring the thermal diffusivity of a material includes a housing having an upper portion and a lower portion, a plate holding the material in a fixed position between the upper portion and lower portion of the housing, and a source at the lower portion of the housing projecting heat onto the material along a first axis that is perpendicular to the plate. A sensor at the lower portion of the housing is movable in relation to the plate and senses the heat radiating through the material along a second axis that is perpendicular to the plate and offset from the first axis. A controller receives data from the sensor and calculates the thermal diffusivity of the material.

23 Claims, 6 Drawing Sheets

(56) References Cited

U.S. PATENT DOCUMENTS

| | | | | |
|---|---|---|---|---|
| 6,419,387 B1* | 7/2002 | Legrandjacques | ........ | G01J 5/10 |
| | | | | 250/332 |
| 7,038,209 B2 | 5/2006 | Opfermann et al. | | |
| 2006/0222047 A1* | 10/2006 | Reading | ................ | B82Y 35/00 |
| | | | | 374/120 |
| 2006/0239328 A1* | 10/2006 | Sumi | ...................... | G01N 25/18 |
| | | | | 374/43 |
| 2008/0224044 A1* | 9/2008 | SempriMoschnig | .. | G01N 25/72 |
| | | | | 250/338.1 |
| 2010/0208242 A1* | 8/2010 | Mart Nez | ............ | G01B 21/085 |
| | | | | 356/72 |
| 2014/0036955 A1 | 2/2014 | Brunner et al. | | |
| 2014/0301424 A1* | 10/2014 | Adamczyk | ............. | G01N 25/20 |
| | | | | 374/44 |

\* cited by examiner

3D DIFFUSIVITY

FIELD OF THE INVENTION

The present teachings relate generally to measurement systems and methods and, more particularly, to systems and methods for measuring three-dimensional (3D) diffusivity.

BACKGROUND OF THE INVENTION

Thermal diffusivity is a measurement of the ability of a material to conduct thermal energy relative to its ability to store thermal energy. It may be calculated using the material's thermal conductivity (W/(m·K)) divided by its density ($kg/m^3$) and specific heat capacity (J/(kg·K)). As an example, heat moves rapidly through a substance with high thermal diffusivity because the substance conducts heat quickly relative to its volumetric heat capacity.

Thermal diffusivity may be measured using the "flash" method. This involves heating a sample of material (e.g., a strip or cylindrical sample, etc.) with a short energy pulse (e.g., heat source such as a light beam, laser, etc.). The temperature change in the sample may then be measured over time.

The assignee of the present application is a manufacturer of flash systems used to measure thermal diffusivity. One such system is the LFA 447 NanoFlash®. The LFA 447 is a compact measuring system, with the flash lamp, sample plate, and sensor vertically arranged. Samples of material are placed on an automatic sample changer, which can test up to four samples. Using the LFA 447, a first side of a sample of material is heated by a short light pulse. The resulting temperature rise on the sample's other side is measured using an infrared sensor. By analyzing the resulting temperature-versus-time curve, the thermal diffusivity of the sample of material can be determined.

U.S. Pat. Pub. 2014/0036955 to Brunner discloses a device and method for the photothermic investigation of a sample. It uses a sample holder that is movable in relation to a fixed optical excitation/detection path. U.S. Pat. No. 6,273,603 to Cheindline discloses a measuring head for use in radiant energy flash measuring of the thermal diffusivity of samples. It uses a movable sample holder and a fixed side view detector, which requires a mirror moving in three coordinates to reflect light from the sample. Neither of these references, the contents of which are incorporated by reference in their entirety, discloses use of a mask.

However, known systems for measuring thermal diffusivity have a number of deficiencies, including that they only provide for testing a sample through the thickness of the sample. Therefore, it would be beneficial to have a superior system and method for measuring 3D diffusivity.

SUMMARY OF THE INVENTION

The needs set forth herein as well as further and other needs and advantages are addressed by the present embodiments, which illustrate solutions and advantages described below.

The system of the present embodiment includes, but is not limited to, a housing having an upper portion and a lower portion, a plate holding the material in a fixed position between the upper portion and lower portion of the housing, and a source at the lower portion of the housing projecting heat onto the material along a first axis that is perpendicular to the plate. A sensor at the upper portion of the housing is movable in relation to the plate and senses the heat projected onto the material. A controller receives data from the sensor and calculates the thermal diffusivity of the material.

In another embodiment the system includes, but is not limited to, a housing having an upper portion and a lower portion, a plate holding the material in a fixed position between the upper portion and lower portion of the housing, and a source at the lower portion of the housing projecting heat onto the material along a first axis that is perpendicular to the plate. A sensor at the upper portion of the housing is movable in relation to the plate and senses the heat radiating through the material along a second axis that is perpendicular to the plate and offset from the first axis. A controller receives data from the sensor and calculates the thermal diffusivity of the material.

In a further embodiment the system includes, but is not limited to, a housing having an upper portion and a lower portion, a plate holding the material in a fixed position between the upper portion and lower portion of the housing, and a source at the lower portion of the housing projecting heat onto the material along a first axis that is perpendicular to the plate. A sensor at the upper portion of the housing is movable in relation to the plate. The sensor senses the heat radiating through the material along the first axis and shifts focus of the sensor to sense the heat radiating through the material along a second axis that is perpendicular to the plate and offset from the first axis. A controller receives data from the sensor and calculates the thermal diffusivity of the material.

Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION OF THE INVENTION

Figure 1:
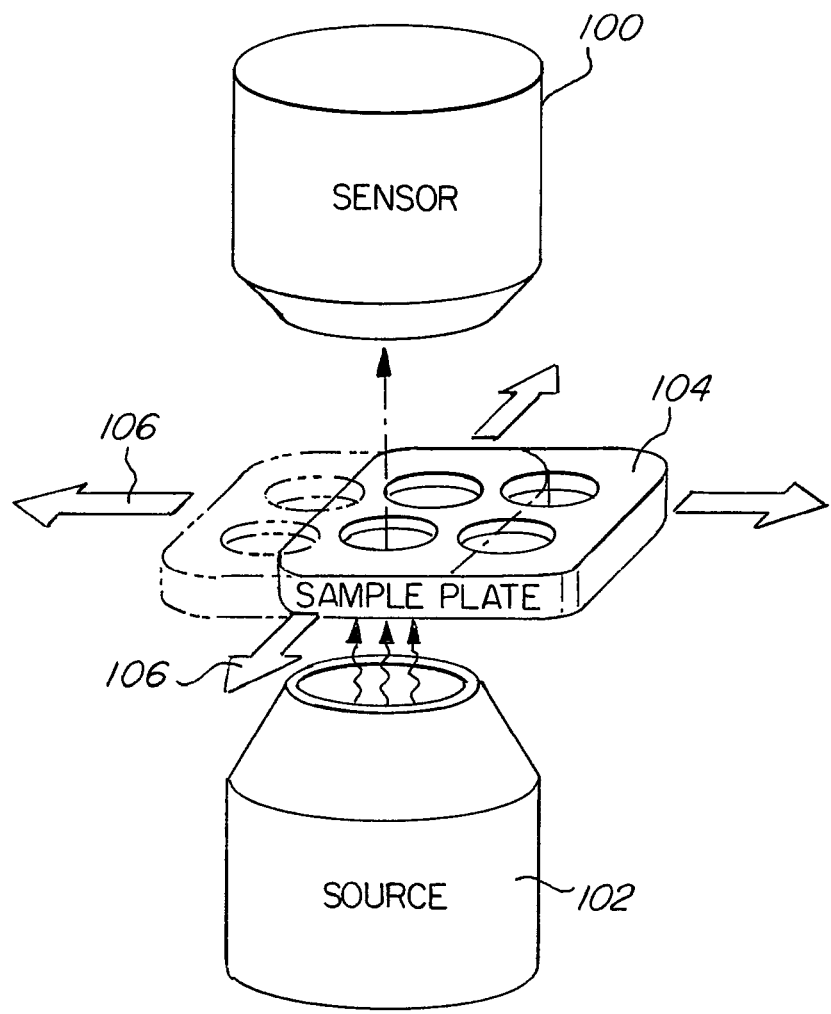
FIG. 1 depicts a system for measuring thermal diffusivity known in the prior art.

The present teachings are described more fully hereinafter with reference to the accompanying drawings, in which the present embodiments are shown. The following description is presented for illustrative purposes only and the present teachings should not be limited to these embodiments. For purposes of explanation and not limitation, specific details are set forth such as particular techniques, etc., in order to provide a thorough understanding. In other instances, detailed descriptions of well-known methods are omitted so as not to obscure the description with unnecessary detail.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second" etc. for different features/components of the present disclosure are only intended to distinguish the features/components from other similar features/components and not to impart any order or hierarchy to the features/components.

Testing of thermal diffusivity may be desirable in any number of different fields. For example, it may be desirable to determine how to improve the heat transfer of an electronic component. It may also be desirable to determine the optimum materials for a heat exchanger system in order to achieve a required efficiency. It may also be desirable to determine the heating/cooling load of a building as a function of weather conditions in order to determine how building materials can be improved. It may also be desirable to determine how fast an aluminum ingot solidifies, how to minimize thermal stresses within a steel block, how to optimize the manufacturing of glass bottles, how fast ceramic components in a catalytic converter heat up, how to select the correct heat exchanger material for the thermal control of a processor, etc. One skilled in the art would appreciate the various applications for the present teachings, which are not limited to any particular embodiments disclosed herein.

Accordingly, measuring heat transfer is important not only in many scientific areas but in many industrial ones as well. For example, when cooling casts, metals, semiconductors, etc., from a liquid phase into a solid state, the heat transfer can have a major impact on the thermophysical properties of the solid. A variety of materials, whether made of chemicals or mixtures, have a homogenous composition. For those materials, the thermal conductivity is a true physical property, depending on temperature, pressure and composition. However, particularly in the solid state, the thermal diffusivity and thermal conductivity also depend on the direction of the heat flow. Such challenges, and many others, cannot be met without accurate knowledge about the thermal properties of diffusivity and conductivity.

The flash technique is a preferable choice for measuring thermal diffusivity by providing a noncontact test method having easy sample preparation, fast testing times, and high accuracy. It can also cover a broad range of applications and temperatures, including from −125° C. up to 2800° C., although not limited thereto.

In practice, one surface of a sample may be heated by a short energy pulse. From the resulting temperature change (e.g., dissipation) measured on the opposite surface (e.g., using an infrared (IR) sensor), the thermal diffusivity may be calculated. In addition, the specific heat of the sample may be calculated and combining these thermophysical properties with the density value results in the thermal conductivity:

$$\lambda(T)=a(T)\cdot cp(T)\cdot \rho(T)$$

where $\lambda$=thermal conductivity [W/(m·K)], a=thermal diffusivity [mm$^2$/s], cp=specific heat [J/(g·K)], $\rho$=bulk density [g/cm$^3$].

Referring now to FIG. 1, shown is a system for measuring thermal diffusivity known in the prior art. The sensor 100 and source 102 (e.g., may be a heat source) are fixed on a central axis of a sample. The sample is fixed in a sample plate 104. As shown, the sample plate 104 may be capable of holding multiple samples. Each sample may be in the shape of a disk, although other shapes would be appreciated by one skilled in the art.

Each disk has a central axis at (or near) its center point, the center axis generally orthogonal to the plane of the disk (also perpendicular to the plate). Movement 106 of the sample plate 104 is restricted to a single preset position on each sample such that a central axis of the sample is on the same axis as the sensor 100 and source 102. As a result, such known systems only provide for testing a sample in a single direction through the thickness of the sample.

In particular, due to limited movement (e.g., four positions for each of the four samples shown), such known systems do not allow a user to measure diffusivity through the plane of the sample (e.g., radially outward from the sample's central axis).

It is desirable to test diffusivity beyond that provided in the prior art. Specifically, it is desirable to measure diffusivity through the plane of the sample to analyze a direction of heat flow and determine a path of diffusivity. This is accomplished according to one embodiment of the present teachings by shifting the sensor so that it is offset from the axis where the heat hits the sample. Improved movement in the present system allows for slight changes so that the sensor and/or source can be moved to various points on the sample. Adjustable optics also provide for improved detection by allowing the system to vary the size of the area being tested on the sample.

The present teachings are desirable for a number of end-users, including universities, research labs, and materials manufacturers, although not limited thereto. They can be used to test any number of different materials, including plastics, ceramics, metals, composites, and multi-layer systems, etc. In an increasingly competitive technological environment, efficiently devised heat transfer processes are desirable. A system according to the present teachings allows for the consideration of radial and facial heat losses through a sample of material in any number of directions.

In addition, finite pulse effects can be comprehensively analyzed using advanced mathematical regression routines. Using multi-property measurement capabilities, both thermal diffusivity and specific heat can be determined simultaneously—on the same sample—thus yielding thermal conductivity if the density is known.

Figure 2:
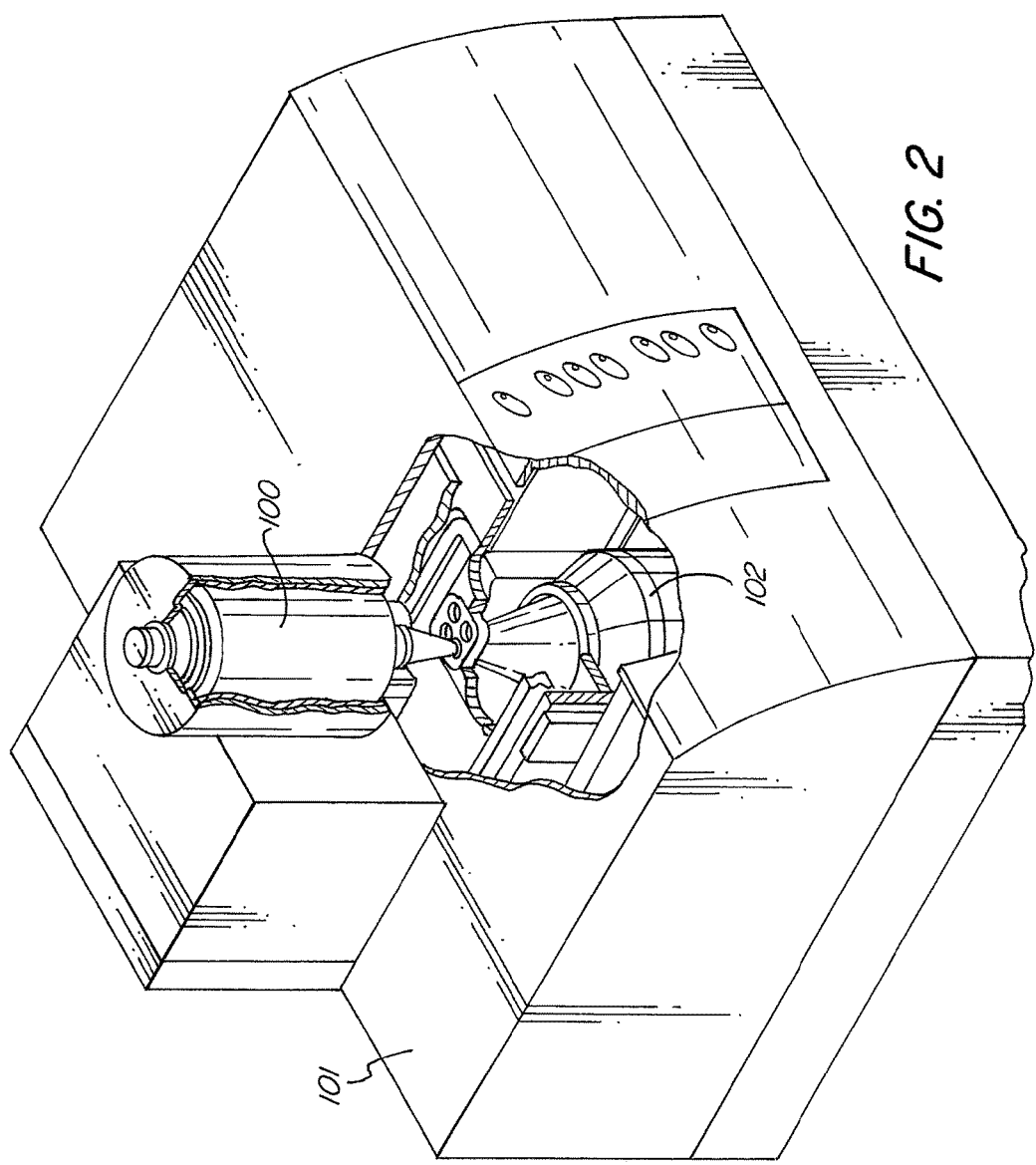
FIG. 2 depicts one embodiment of a system for measuring 3D diffusivity according to the present teachings.

Referring now to FIG. 2, shown is one embodiment of a system for measuring 3D diffusivity according to the present teachings. The system may be designed as a unitary system in a housing 101, although it is to be appreciated that the housing 101 may comprise separate components (e.g., multiple housing elements). It may be designed as a vertical system with a source 102 at a bottom portion of the housing and a sensor 100 at an upper portion of the housing, although not limited thereto. Such a system provides a fast, non-contact, and efficient method for measuring the thermophysical properties of thermal diffusivity, specific heat capacity, and thermal conductivity. The data acquisition rate of both the sensor and pulse mapping channels may be 2 MHz or more. Thereby, highly conductive and/or thin materials requiring very short test times can be reliably measured.

Figure 3:
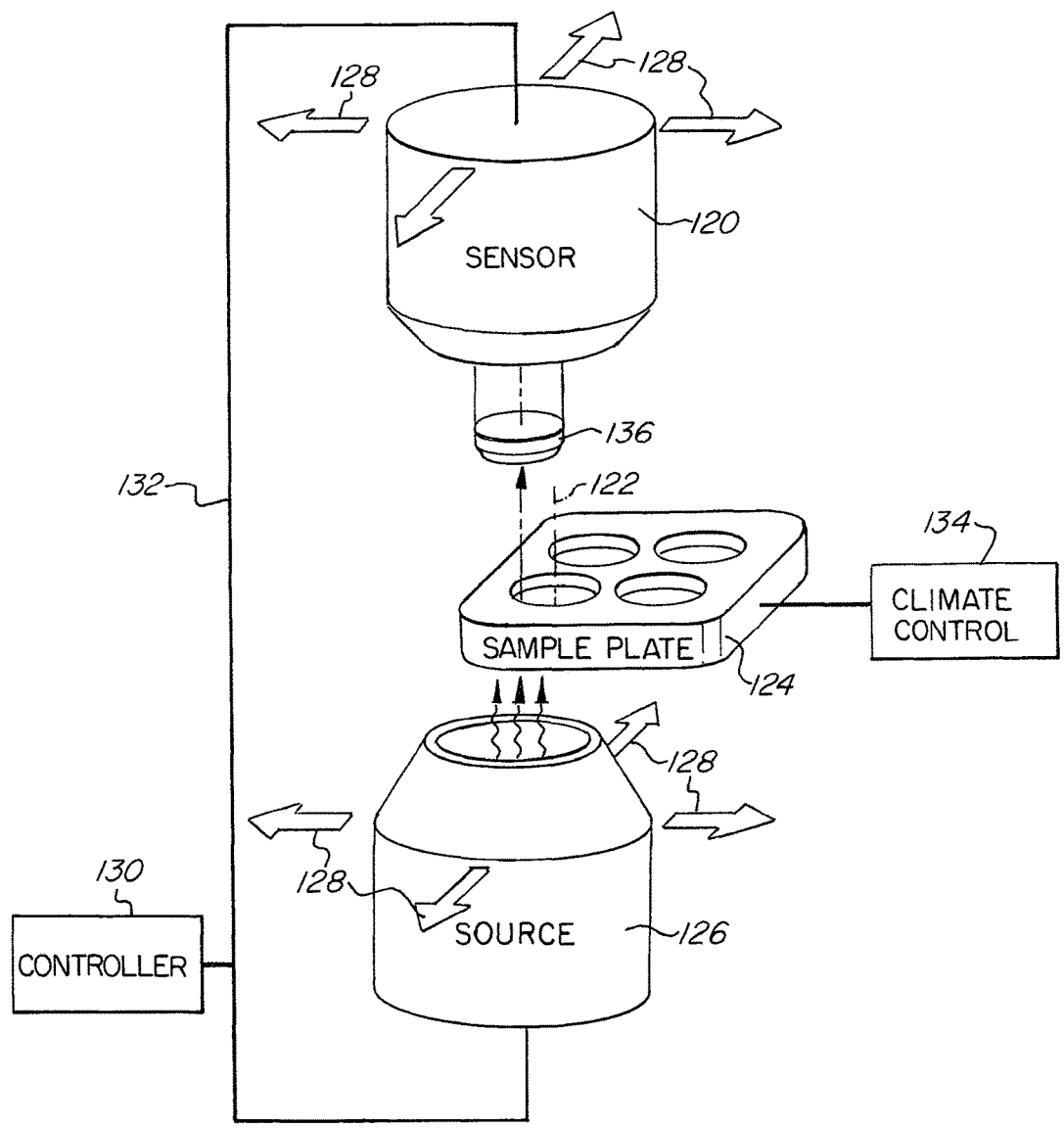
FIG. 3 depicts one embodiment of the system of FIG. 2.

Referring now to FIG. 3, shown is one embodiment of the system of FIG. 2. As shown, the sensor 120 is offset from a central axis 122 of a sample of material that is held by the sample plate 124 (discussed further below in relation to FIG. 4). Such a configuration allows for the measuring of 3D diffusivity. For example, heat may be projected at the material and radiate along axis 122, whereas the sensor 120 may be moved at various positions offset from the axis 122.

This allows for analysis of expansion, conductivity (how much heat), diffusivity (how fast heat dissipates), etc., in order to measure a "path" of diffusivity through the sample, although not limited thereto.

The sensor 120 and source 126 may each move 128 independently or together (when joined by a frame 132, housing, or similar structure). Movement may be controlled by a controller 130 in order to provide small movements so that diffusivity can be measured at various places on the sample.

In one embodiment, a xenon lamp may serve as the source 126 and provide heat to the sample of material. The source 126 may be user-exchangeable and have a long lifetime. Variable pulse energy may be controlled by the controller 130, for example, up to 10 Joule/pulse, although not limited thereto. The pulse width may also be adjustable, for example, 20 to 1200 μs. A filter wheel can be used for further adjustments.

In one embodiment, the sensor 120 may be an indium antimonide (InSb) sensor. This may be suitable for measuring room temperatures up to 500° C., although not limited thereto. In another embodiment, a mercury cadmium telluride (MCT) sensor may be used. This may allow for measurements from −100° C. to 500° C. (prior systems could only go up to 200° C.), although not limited thereto. Such a design may ensure that even at cryogenic temperatures measurements are based on the energy radiation from the sample's surface. In addition, the sensor 120 may be equipped with optional liquid nitrogen auto-refill system, which may be useful for long running tests without operator intervention.

Figure 4:
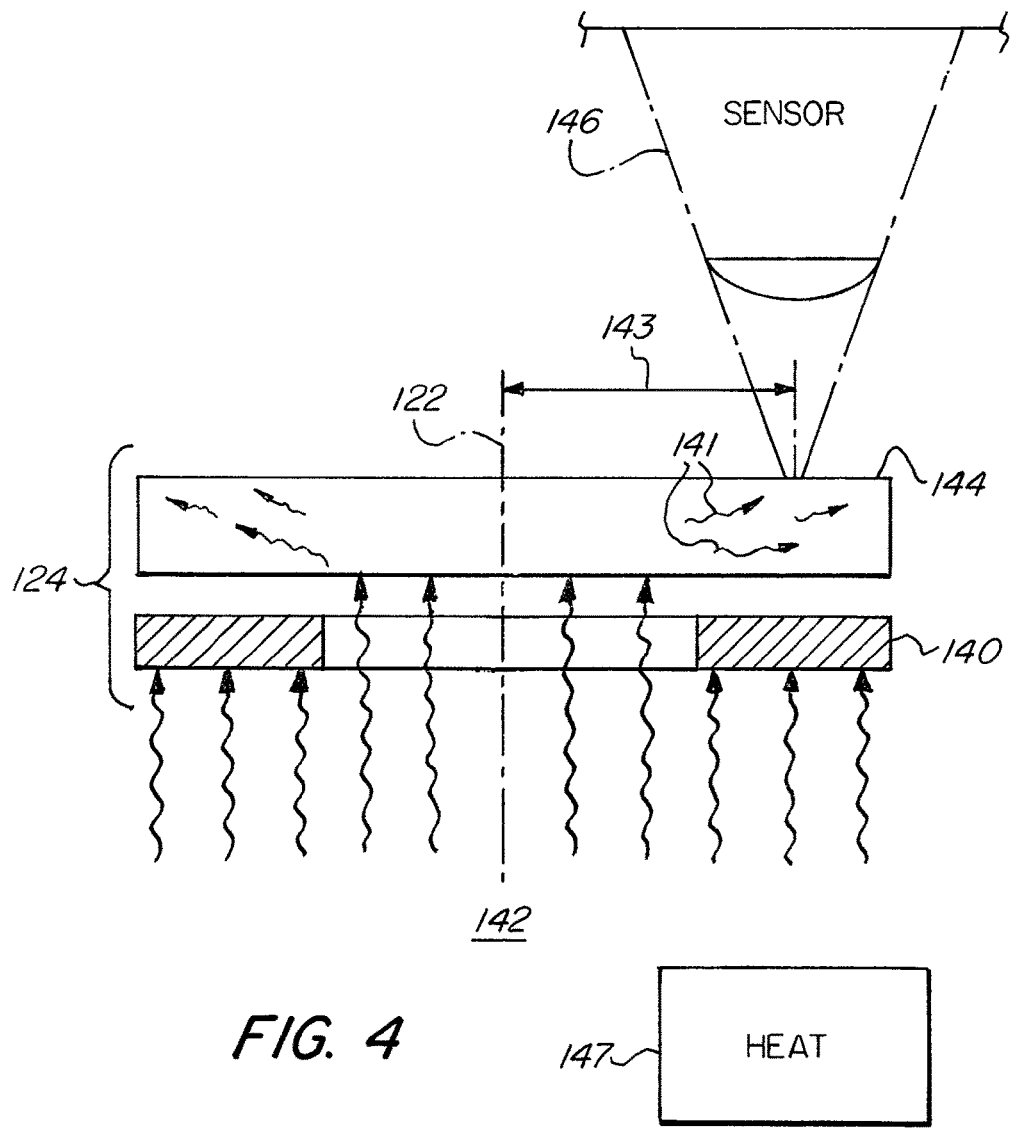
FIG. 4 depicts an enlarged view of one embodiment of a sample plate according to FIG. 3.

In one embodiment, the sensor 120 may comprise an actuated lens 136 (e.g., zoom lens, etc.) to optimize and focus the sensor 146 (shown in FIG. 4). With a vertical configuration of the system, the actuated lens 136 may only need to move in one direction, e.g., orthogonal to the plane of the sample 144. This may reduce the complexity of components and the potential for error, although not limited thereto. Actuation may be provided by a stepper motor, although not limited thereto, which may be controlled by the controller 130. The actuated lens 136 may help to avoid signal distortions from surroundings of the sample 144, such as masks 140 or aperture stops. This may be particularly desirable for samples having a small diameter. It also helps ensure that the sensor 120 is kept within its linear responsivity range.

In known prior art systems, the sensor field of view is fixed and made large enough to accommodate large-diameter samples. When testing smaller diameter samples, however, aperture stops are commonly used in an attempt to minimize the influence of the surroundings. This often results in a significant distortion of the thermal curve to the extent that the sensor not only senses the temperature excursion of the sample, but also any fluctuations from the aperture stop. Consequently, a thermal curve may show either a continuously increasing trend or an extended leveling-off period.

In the present teachings, an actuated lens 136 (e.g., zoom lens, etc.) helps ensure that a heat signal originates solely from the sample surface and not from any surrounding parts. Therefore, both large and small samples can be tested by narrowing focus of the sensor 146 (shown in FIG. 4). This is particularly helpful because in contrast with prior art systems, the sensor according to the present teachings can be offset from where the heat is projected onto the material (e.g., near an edge of the material to measure a thermal diffusivity path as heat radiates). Whereas in known systems an aperture stop could produce noticeable effects, the thermal curve according to the present teachings conforms to the theoretical model, yielding correct diffusivity values.

Moreover, an actuated lens in one embodiment may be used to shift (e.g., angle) the focus of the sensor 146 (shown in FIG. 4) so that it is offset from where the heat reaches the material (e.g., heat radiates along axis 122). In this case, the sensor 120 and source 126 may be fixed together on the same axis, which may be a central axis 122 of the sample 144. But since the actuated lens can move and focus the sensor 146 so that it is offset from axis 122 no mask may be needed.

Referring now to FIG. 4, shown is an enlarged view of one embodiment of a sample plate 124 according to FIG. 3. The plate 124 may include a "mask" 140 (also shown in FIG. 5). A mask may be used to direct the heat to a particular location on the sample. For example, the mask 140 may allow heat 142 from a source 147 to reach a sample 144 and radiate along a central axis 122, but may otherwise block the heat from reaching the sample 144 at other areas.

As a result, the mask allows the sensor 120 and source 126 (shown in FIG. 3) to be fixed on the same axis with each other (e.g., with a frame 132) so that they both can be positioned at an offset 143 from where heat is projected onto the material (e.g., heat radiates along axis 122) and measure 3D diffusivity. The system can measure diffusivity in various directions 141 through the sample (e.g., no longer limited to measuring diffusivity only through its axis 122 but can measure 3D diffusivity).

It may be preferable to have the sensor 120 and/or the source 126 move while the sample plate 124 remains fixed. This way, there is less chance that a sample may shift in the sample plate 124 (e.g., sample may be a liquid, etc.) when taking measurements from different axes on the sample.

Figure 5:
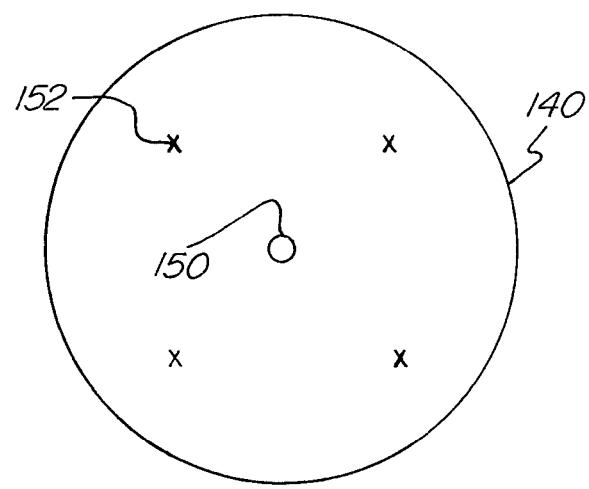
FIG. 5 depicts one embodiment of a mask according to FIG. 4.

Referring now to FIG. 5, shown is one embodiment of a mask 140 according to FIG. 4. As shown, the mask 140 may be shaped to correspond with the shape of a sample 144 (shown in FIG. 4), although not limited thereto. The mask 140 may have an opening 150 to allow heat 142 to reach the sample 144. As a result, even if the source 147 is positioned offset from a central axis 122 of the sample 144, the heat 142 will be directed to the opening 150 so that 3D diffusivity can be measured at other points 152.

Figure 6:
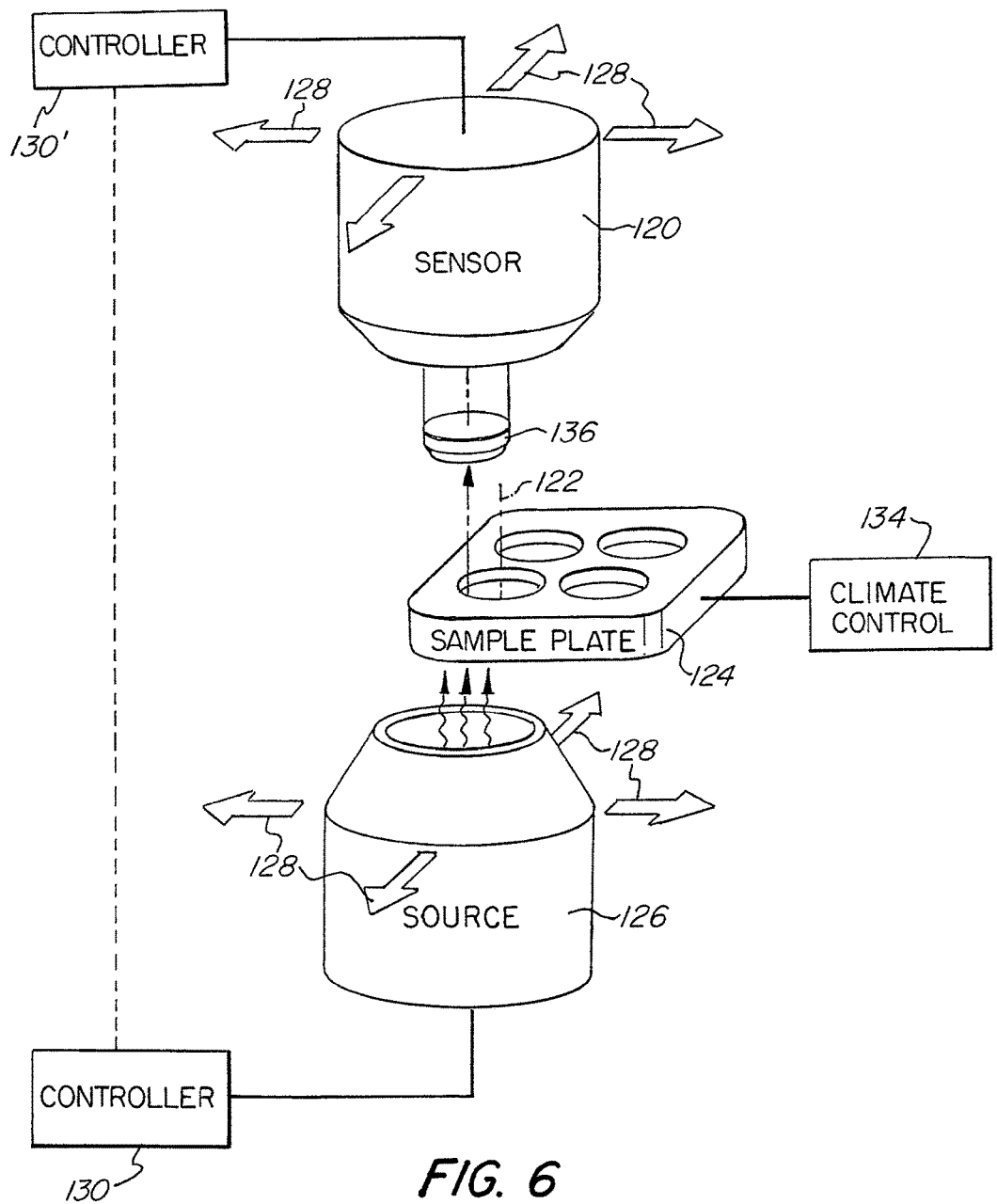
FIG. 6 depicts one embodiment of the system of FIG. 2 where the sensor and source may be moved separately.

Referring now to FIG. 6, shown is one embodiment of the system of FIG. 2 where the sensor 120 and source 126 may be moved separately. One or more controllers 130,130' may position the sensor 120 and source 126. In this way, the sensor 120 may be focused offset from axis 122 of the sample 144 while the source 126 is positioned on the axis 122 (or at some other axis) of the sample 144 to measure 3D diffusivity without the need for a mask 140.

The controller 130 (also shown in FIG. 3) may have software to carry out measurements and evaluate the resulting data. User-friendly menus combined with automated routines may provide sophisticated analysis. Some features may include:

Comparative analysis for series of shots from the same database (e.g., up to 32 or more)

Loading of series of single shots with a preview of parameters and temperature program Storage of results for subsequent restoration and analysis Graphic export: EMF, PNG, BMP, JPG, TIF, or PDF; ASCII-file, export into Excel®-compatible CSV-format Model wizard including F-test for selecting of the best model fit Definition of an arbitrary number of temperature levels and number of shots per level General Key Software Features Determination of specific heat with a comparative method Integrated database Determination of contact resistance in multi-layer systems Graph of the measurement curves (e.g., up to 3 or more scalable Y axes)

Fast zoom function for X and Y segments

Measurement values shown as a Tool-Tip when moving the mouse over the measurement points Thermal diffusivity graphs as a function of temperature or time Calculation and graph of the cp-curve Combined graph of raw data and theoretical model Thermal resistance calculation (2-layer model)

Support for different displays

The controller 130 may have various calculation models, corrections and mathematical operations. For thermal diffusivity under various boundary conditions, different baselines/models with correction of the pulse width may be used, including:

Adiabatic

Cowan

Improved Cape-Lehman (through consideration of multidimensional heat loss and non-linear regression)

2-/3-layer models (analysis by means of non-linear regression and consideration of heat loss)

In-plane

Radiation correction (for transparent and semi-transparent samples)

Heat-loss corrections

Accurate pulse length correction, pulse mapping

Baseline correction

Multiple-shots averaging

Shot approximation via various mathematical functions (polynomials, splines, etc.)

Classical models such as Parker, Cowan 5, Cowan 10, Azumi, Clark-Taylor

A system according to the present teachings provides for thermal characterization of high conductivity materials at cryogenic and moderate temperatures, or ceramics and refractories at elevated temperatures, although not limited thereto. Measurements from −125° C. (e.g., below the glass transition temperature of rubber materials) to 2800° C. can be readily carried out with a single instrument setup, without the need for swapping a furnace or cooling device. However, different furnaces and cooling systems may be used with the modular system.

A climate control device 134 (shown in FIGS. 4 and 6) may provide for control of heat (e.g., a furnace), cold (e.g., cooling device), pressure, and/or a gas-filled environment, although not limited thereto. A furnace may provide for measurements up to 500° C. and higher, although not limited thereto. The design of the furnace enables thermal coupling to different cooling devices. This may reduce the measurement times and allow for heating rates up to 50 K/min or more, while maintaining an excellent thermal stability, although not limited thereto. Cooling devices using liquid nitrogen may allow for temperatures of −100° C. and lower, although not limited thereto. Depending on a purge gas and sample, lower temperatures can be achieved.

Using the climate control device 134, the cooling systems can be operated with the evacuation system running (below atmospheric pressure). This leads to a further reduction in heat loss and convection. However, a cooling system can also be operated during measurements under a defined atmosphere using a purge gas. This is advantageous when testing oxygen-sensitive samples. The atmosphere can also be controlled via integrated frits or via mass flow controllers both for one protective and two purge gases. All gas controls may offer operation in oxidizing, inert, dynamic or static atmospheres. Additionally, pumping allows for measurements under reduced pressure.

In one embodiment, a sample plate may carry round or square samples with a diameter of 12.7 mm each. For measurements on larger samples, inserts can be chosen to accommodate diameters of up to, for example, 25.4 mm or more. Depending on the sample's properties, its thickness can vary between 0.01 mm and 6 mm, although not limited thereto.

In addition to the standard sample plates for solid samples of round and square geometries, other sample plates may be used for special applications on specific materials, including: molten polymers and low viscosity liquids, resins during curing, pastes and powders, fibers, laminates, etc. In a sample plate for liquids, for example, continuous contact between the liquid and a crucible may be assured over the entire temperature range—even at freezing temperatures. Heat transfer through the container wall may be minimized. Another sample plate may be used for measurements on resins during the curing process. In addition, sample plates for measurements under mechanical pressure may be used. One skilled in the art would appreciate the different shapes, sizes, and structures that may be used to construct sample plates according to the present teachings, which are not limited to any particular embodiments disclosed herein.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A system for measuring the thermal diffusivity of a material, comprising:
a housing having an upper portion and a lower portion;
a plate holding the material in a fixed position between the upper portion and lower portion of the housing;
a source at the lower portion of the housing projecting heat onto the material along a first axis that is perpendicular to the plate;
a sensor at the upper portion of the housing and movable in relation to the plate, the sensor sensing the heat projected onto the material;
a controller receiving data from the sensor and calculating the thermal diffusivity of the material;

the sensor sensing the heat radiating through the material along a second axis that is perpendicular to the plate, the second axis offset from the first axis.

2. The system of claim 1, wherein the sensor senses the heat radiating through the material along the first axis.

3. The system of claim 1, wherein the sensor moves in small increments to sense the heat that radiates along a plurality of axes through the material in order to measure a path of the flow of heat through the material.

4. The system of claim 1, further comprising:
a mask between the material and the source, the mask having an opening and a closed portion, the opening allowing the heat to reach the material along the first axis, the closed portion blocking the heat from reaching the material;
wherein the source is positioned offset from the first axis.

5. The system of claim 4, wherein the source moves together with the sensor in relation to the plate.

6. The system of claim 1, further comprising:
an actuated lens that shifts focus of the sensor to sense the heat radiating through the material along the second axis.

7. The system of claim 1, further comprising:
an actuated lens narrowing focus of the sensor on the material.

8. The system of claim 7, wherein the actuated lens comprises a zoom lens.

9. The system of claim 7, wherein the actuated lens comprises a stepper motor.

10. The system of claim 1, wherein the controller controls movement of the sensor.

11. The system of claim 1, wherein the source is movable in relation to the material, and the source and sensor each move independently from one another.

12. The system of claim 1, further comprising a climate control device adapted to cool the material to −125° C. and heat the material to 2800° C.

13. The system of claim 1, wherein the controller calculates thermal conductivity of the material using the calculated thermal diffusivity.

14. A system for measuring the thermal diffusivity of a material, comprising:
a housing having an upper portion and a lower portion;
a plate holding the material in a fixed position between the upper portion and lower portion of the housing;
a source at the lower portion of the housing projecting heat onto the material along a first axis that is perpendicular to the plate;
a sensor at the upper portion of the housing and movable in relation to the plate, the sensor sensing the heat radiating through the material along a second axis that is perpendicular to the plate and offset from the first axis;
a controller receiving data from the sensor and calculating the thermal diffusivity of the material.

15. The system of claim 14, wherein the source moves together with the sensor in relation to the plate.

16. The system of claim 15, further comprising:
a mask between the material and the source, the mask having an opening and a closed portion, the opening allowing the heat to reach the material along the first axis, the closed portion blocking the heat from reaching the material.

17. The system of claim 14, further comprising an actuated lens that shifts focus of the sensor to sense the heat radiating through the material along the second axis.

18. The system of claim 14, wherein the offset is less than 1 centimeter.

19. The system of claim 14, wherein the source comprises a xenon lamp.

20. The system of claim 14, wherein the sensor comprises an indium antimonide sensor or a mercury cadmium telluride sensor.

21. A system for measuring the thermal diffusivity of a material, comprising:
a housing having an upper portion and a lower portion;
a plate holding the material in a fixed position between the upper portion and lower portion of the housing;
a source at the lower portion of the housing projecting heat onto the material along a first axis that is perpendicular to the plate;
a sensor at the upper portion of the housing movable in relation to the plate, the sensor sensing the heat radiating through the material along the first axis and shifting focus of the sensor to sense the heat radiating through the material along a second axis that is perpendicular to the plate and offset from the first axis;
a controller receiving data from the sensor and calculating the thermal diffusivity of the material.

22. The system of claim 21, wherein the sensor moves in small increments to sense the heat that radiates along a plurality of axes through the material in order to measure a path of the flow of heat through the material.

23. The system of claim 21, wherein the plate holds a plurality of materials, and the source is movable in relation to the plate to project heat onto each of the plurality of materials.

* * * * *